US006656462B2

(12) United States Patent
Dondero et al.

(10) Patent No.: US 6,656,462 B2
(45) Date of Patent: Dec. 2, 2003

(54) INTERLEUKIN-1 MUTEINS USEFUL AS VACCINE ADJUVANTS

(76) Inventors: Richard S. Dondero, 37 Hillside Ave., Riverdale, NJ (US) 07457; Herman F. Staats, 6106 Bent Oak Dr., Durham, NC (US) 27705

(*) Notice: Subject to any disclaimer, the term of this patent is extended or adjusted under 35 U.S.C. 154(b) by 0 days.

(21) Appl. No.: 09/729,509

(22) Filed: Dec. 4, 2000

(65) Prior Publication Data

US 2001/0036452 A1 Nov. 1, 2001

Related U.S. Application Data

(60) Provisional application No. 60/168,928, filed on Dec. 3, 1999.

(51) Int. Cl.$^7$ ........................ A16K 38/19; A16K 38/16; C07K 14/52
(52) U.S. Cl. ................. 424/85.2; 424/85.1; 530/351; 514/2; 514/8; 514/21; 514/885; 435/69.5; 435/69.52
(58) Field of Search ................ 424/85.2, 85.1; 530/351; 435/69.5, 69.52; 514/2, 8, 21, 885

(56) References Cited

U.S. PATENT DOCUMENTS

| 5,206,014 A | 4/1993 | Nencioni et al. ............. 424/88 |
| 5,286,847 A | 2/1994 | Gehrke et al. ............. 424/85.2 |
| 5,334,379 A | 8/1994 | Pillai et al. ................ 424/85.4 |
| 5,503,841 A | 4/1996 | Doyle et al. ............. 424/278.1 |
| 5,847,098 A | 12/1998 | Nakai et al. ............... 536/23.5 |

FOREIGN PATENT DOCUMENTS

WO  9101143  7/1990

OTHER PUBLICATIONS

Carter, D.B., M.R. Deibel, C.J. Dunn et. al. (Apr. 1990) "Purification, cloning, expression and biological characterization of an interleukin–1 receptor antagonist protein" *Nature* 344:633–638.
Clore, G.M., P.T. Wingfield, A.M. Gronenborn (1991)"High–Resolution Three–Dimesional Structure of Inteleukin 1β In Solution by Three–and Four–Dimensional Nuclear Magnetic Resonance Spectorscopy" *Biochemistry* 30(9):2315–2323.
DeChiara, T.M., Young, D., et. al. (Nov. 1986) "Structure–function analysis of murine interleukin 1:Biologically active polypeptides are at least 127 amino acids long and are derived from the carboxyl terminus of a 270–amino acid precursor" *Proc. Natl. Acad. Sci.* 83:8303–8307.
Dower, S.K. et al., (Aug. 1985) "Detection and Characterization of High Affinity Plasma Membrane Receptors for Human Interleukin 1" [1985] *J. Exp. Med.* 162:501–515.

Dripps, D.J., B.J. Brandhuber, R.C. Thompson, S.P. Eisenberg (Jun. 5, 1991) "Interleukin–1 (IL–1) Receptor Antagonist Bonds to the 80–kDa IL–1 Receptor but Does Not Initiate IL–1 Signal Transduction" *J. Biol. Chem.* 266(16):10331–10336.
Driscoll, P.C., G.M. Clore, D. Marion, et. al. (1990) "Complete Resonance Assignment for the Polypeptide Backbone of Interleukin 1β Using Three–Dimensional Heteronuclear NMR Spectroscopy" *Biochemistry* 29(14):3542–3556.
Finzel, B.C. et. al. (1989) "Crystal Streucture of Recombinant Human Interleukin–1β at 2• Å Resolution" *J. Mol. Biol.* 209:779–791.
Graves, B.J., M.H. Hatada, W.A. Hendrickson,, J.K. Miler, V.S. Madison, Y. Satow (1990) "Structure of 1α at 2.7–Å Resolution" *Biochemistry* 29:2679–2684.
Gronenborn, et. al. (Apr. 1998) "Site directed mutants of human interleukin–1α: a H–NMR and receptor binding study" *Federation of European Biochemical Societies* 231(1):135–138.
Hannum, C.H., C.J. Wilcox, W.P. Arend et. al. (Jan. 1990) "Interleukin–1 receptor antagonist activity of human interleukin–1 inhibitor" *Nature* 343:336–340.
Huang, J.J. et. al. (Nov. 1987) "Muteins of human interleukin–1 that show enhanced bioactivities" *FEBS Letters* 223(2):294–298.
Jobling, Stephen A., Philip E. Auron, Gary Gurka et. al. (Nov. 5, 1988) "Biological Activity and Receptor Binding of Human Prointerleukin–1β and Subpeptides" *J. Biol. Chem.* 263:16372–16378.
Ju, G., E. Labriolatompkins, C.A. Campen, et. al. (Apr. 1991) "Conversion of the interleukin 1 receptor antagonist into an agonist by site–specific mutagenesis" *Proc. Natl. Acad. Sci. USA* 88:2658–2662.
Kramer, D.R., R.M. Sutherland, S. Bao and A.J. Husband (1995) "Cytokine mediated effects in mucosa immunity" *Immunology and Cell Biology* 73:389–396.
Lin et. al. (Dec. 1995) "Present Status of the Use of Cytokines as Adjuvants with Vaccines to Protect Against Infectious Diseases" *Clinical Infectious Diseases* 21:14391449.

(List continued on next page.)

*Primary Examiner*—Gary Kunz
*Assistant Examiner*—Fozia Hamud
(74) *Attorney, Agent, or Firm*—Woodcock Washburn LLP

(57) ABSTRACT

The present invention concerns compositions comprising an IL-1 mutein that is useful as an adjuvant for stimulating a controlled immune response when administered to a human or animal. For example, muteins of IL-1β can be used according to the invention. The mutein composition can include a vaccine antigen, such as whole inactivated or attenuated virus, recombinant or synthetic peptides, and other antigenic materials.

Figure 1:
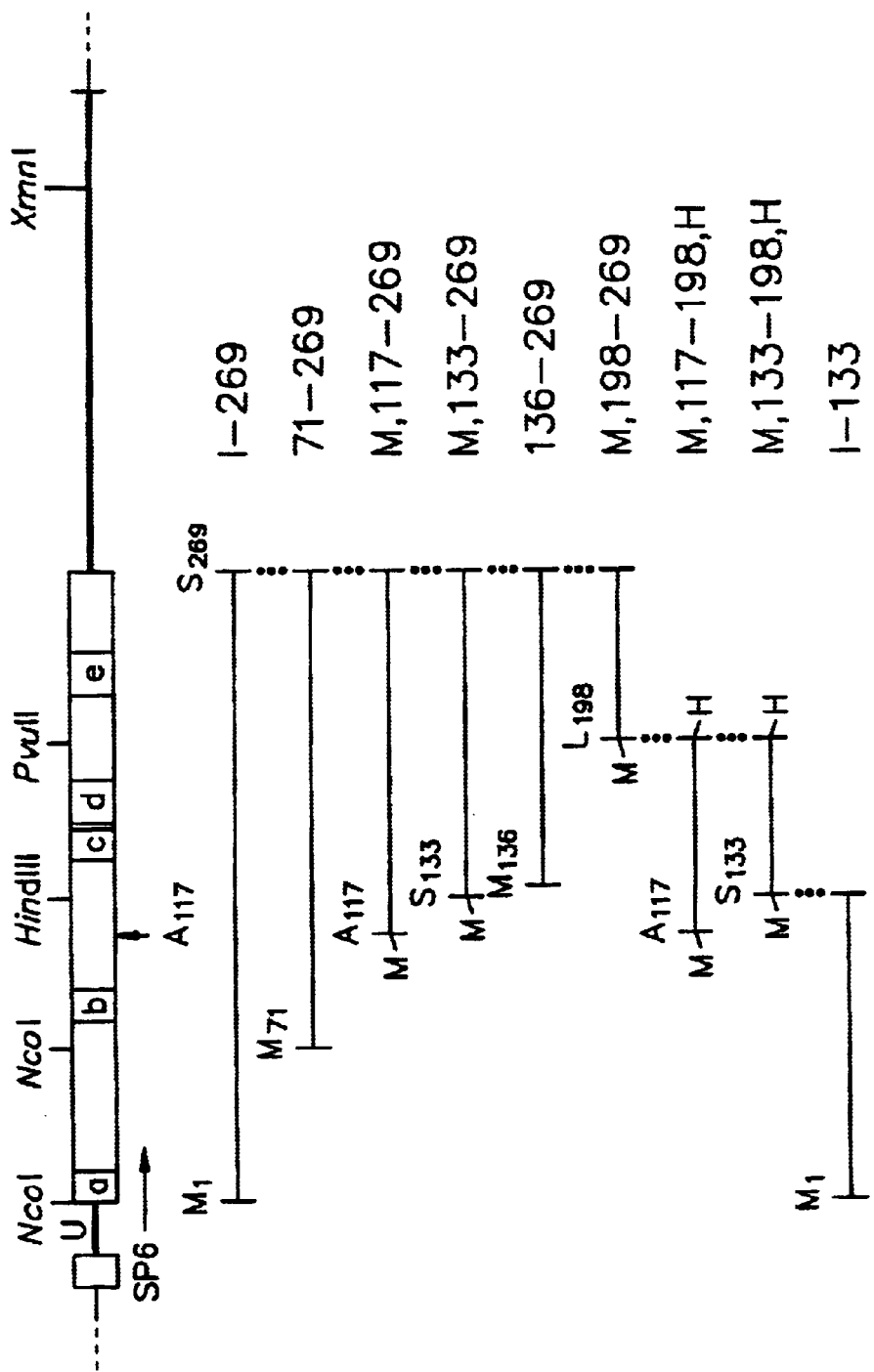

The present invention also pertains to the use of an IL-1 mutein in a human or animal as an adjuvant to increase immune responses to an antigen or other material to which an immune response is desired.

4 Claims, 2 Drawing Sheets

OTHER PUBLICATIONS

Lofthouse, S.A., Andrews, A.E., Barchan, G.J., Nash, A.D. (1995) "Parameters related to the application of recombinant ovine interleukin–1β as an adjuvant" *Vaccine* 13(14):1277–1287.

MacDonald, H. Robson, Paul Wingfield, Ursula Schmeissner et al. (Dec. 1986) "Point mutations of human interleukin–1 with decreased receptor binding affinity" *FEBS Letters* 209(2):295–298.

McMahan, Catherine J., Jennifer L. Slack, Bruce Mosley et. al. "A novel IL–1 receptor cloned from B cells by mammalian expression, is expressed in many cell types" *EMBO J.* 10(10):2821–2832, 1991.

Mosley, Bruce, Steven K. Dower, Steven Gillis, David Cosman (Jul. 1987) "Determination of the minimum polpeptide lengths of the functionally active sites of human interleukins 1α and 1β" *Proc. Natl. Acad. Sci.* 84:4572–4576.

Nash, A.D., S.A. Lofthouse, G.J. Barcham et. al. (1993) "Recombinant cytokines as immunological adjuvants" *Immunology and Cell Biology* 71:367–379.

Priestle, John P., Hans–Peter Schär, and Markus G. Grütter (1990) "The three–dimensional structure of human interleukin–1β refined to 2.0 A resolution" In: *Cytokines and Lipcortins* in Inflammation and Differentiation, 297–307.

Priestle, John P., Hans–Peter Schär and Markus G. Gruütter [1988] "Crystal Structure of the cytokine interleukin–1β" *The EMBO Journal* 7(2):339–343.

Seckinger, Philippe, Karen Williamson, Jean–Francois Balavoine et al. Sep. 1, 1987) "A Urine Inhibitor of Interleukin 1 Activity Affects Both Interleukin 1α and 1β but not Tumor Necrosis Factor $α^1$" *J. Immunol.* 139(5):1541–1545.

Sims, John E., Carl J. March, David Cosman et al. (Jul. 29, 1988) "CDNA Expression Cloning of the IL–1 Receptor, a Member of the Immunoglobulin Superfamily" *Science* 241:585–588.

Spriggs, Melanie K., Pamela J. Lioubin, Jennifer Slack et al. (Dec. 1990) "Induction of an Interleukin–1 Receptor (IL–1R) on Monocytic" *J. Biol. Chem.* 265(36):22499–22505.

Staats, Herman F. and Francis A. Ennis, Jr. (1999) "1L–1 s An Effective Adjuvant for Mucosal and Systemic Immune Responses When Coadministered with Protein Immunogens" *American Association of Immunologies* 162:6141–6147.

Wu, Hong–Yin and Michael W. Russell (1994) "Comparison of systemic and mucosal priming for mucosal immune responses to a bacterial protein antigen given with or coupled to cholera toxin (CT) B subunit, and effects of pre–existing anti–CT immunity" *Vaccine* 12:215.

Young, P., V. Kumar, J. Lillquist et al. (1990) "A site–specific muant of IL–1β with reduced activity but wild–type binding" *Lymphokine Res.* 9:599 (abstract No. 3.55).

Boraschi and Tagliabue, "Interleukin–1 and Interleukin–1 Fragments as Vaccine Adjuvants", *Methods*, 1999, 19, 108–113.

Nakai, S. et al., "A Mutant Protein of Human Interleukin–1β with Immunostimulatory But Not Pyrogenic Potency", *Life Sciences*, 1990, 47, 1707–1714.

Staats and Ennis, "IL–1 Is an Effective Adjuvant for Mucosal and Systemic Immune Responses When Coadministered with Protein Immunogens", *The Journal of Immunology*, May 15, 1999, 162, 6141–6147.

Staats, H.F. et al., "IL–1β Is an Effective Adjuvant for Nasal Vaccines", *Cytokine*, Nov., 1999, 11, 199.

INTERLEUKIN-1 MUTEINS USEFUL AS VACCINE ADJUVANTS

CROSS-REFERENCE TO A RELATED APPLICATION

This application claims the benefit of U.S. Provisional Application No. 60/168,928, filed Dec. 3, 1999.

BACKGROUND OF THE INVENTION

The immune system is regulated in part by a complex network of chemical signals. These signals include the interleukins such as IL-1α and IL-1β. IL-1β is a polypeptide hormone synthesized and secreted by stimulated monocytes. The initial translation product of IL-1β is a 31 kDa precursor polypeptide having relatively low biological activity. After synthesis, the 31 kDa precursor for IL-1β is enzymatically cleaved to its highly active mature form which has a size of about 17.5 kDa. The N-terminus of mature IL-1β derived from human activated monocytes has been characterized by an N-terminal amino acid sequence beginning with Ala-Pro. The N-terminal Ala residue of human mature IL-1β is in the 117 position and an Asp residue is in the 116 position counting from the N-terminus of human precursor IL-1 β polypeptide. Mature IL-1β consists of the C-terminal 153 residues of the precursor polypeptide.

Many physiological actions and biological activities of IL-1β have been identified. IL-1β biological activity is often determined by assaying for stimulation of thymocyte proliferation. IL-1β activities also include stimulation of B-lymphocyte maturation, lymphocyte proliferation, stimulation of fibroblast growth and induction of acute-phase protein synthesis by hepatocytes.

Other biological activities have been attributed to IL-1β polypeptides. These include control of differentiation and activation of lymphocytes, stimulation of lymphokine and prostaglandin production, promotion of inflammation, induction of acute phase proteins, stimulation of bone resorption, and alteration of the level of iron and zinc in blood. Moreover, it has been found that IL-1β can stimulate the hypothalamus-pituitary-adrenal axis, suggesting that IL-1β is integrated in the complex neuroendocrine network that controls homeostasis.

Maturation and release of mature IL-1β from macrophages does not proceed by conventional means normally associated with most secretory proteins because the precursor IL-1β polypeptide lacks a hydrophobic signal sequence. Further, IL-1β is not associated with a membrane-bound compartment in monocytes. Most secretory proteins are characterized by the presence of a hydrophobic stretch of amino acids called a signal sequence. The signal sequence directs the translocation of the protein across the membrane of the endoplasmic reticulum during protein synthesis. The protein is subsequently ushered out of the cell via exocytosis. Most secreted proteins have a signal sequence at the amino terminal that is removed upon translocation. Other proteins, such as ovalbumin, have an internal signal sequence that is not removed upon translocation. The precursor form of IL-1β lacks any region (either amino terminal or internal) with sufficient hydrophobicity and length to qualify as a signal sequence.

It is very likely that the biological activity of IL-1β is tightly linked to the structural integrity of the protein molecule, for deletion of amino acids from the mature protein is accompanied by severe diminution of bioactivity. Several groups have introduced point mutations in an attempt to probe receptor ligand interactions (Jobling et al., 1988; Dechiara, T. M. et al. [1986] *Proc. Natl. Acad. Sci. USA* 83:8303–8307; Mosley, B., S. K. Dower, S. Gillis, D. Cosman [1987] *Proc. Natl. Acad Sci. USA* 84:4572–4576). Huang et al. (Huang, J. J. et al. [1987] *FEBS Letters* 223:294–298) reported that the biological activity of IL-1 β was increased four- to seven-fold by changing the native $NH_2$-terminal sequence from ala-pro-val-arg-serto thr-met-val-arg-ser; however, further alteration of arginine$_{120}$ to generate thr-met-val-glu-ser effectively abolished bioactivity. Circular dichroism data demonstrated no major structural differences among the proteins. Gronenborn et al. (Gronenborn, A. M., P. T. Wingfield, H. F. McDonald, U. Schmeissner, G.M. Clore [1988] *FEBS Letters* 231:135–138) mutated IL-1-alpha histidine and tryptophan residues without effect upon receptor binding affinity, while MacDonald et al. (MacDonald, H. R. et al. [1986] *FEBS Letters* 209:295–298) reported IL-1 histidine muteins with 2–100 fold less competitive binding activity than the wild-type protein.

Excessive or unregulated IL-1 has been implicated in various diseases. These include rheumatoid arthritis (see, e.g., Fontana et al. [1982] *Arthritis Rheum.* 22:49–53); osteoarthritis (see, e.g., Wood et al. [1983] *Arthritis Rheum.* 26:975); toxic shock syndrome (see, e.g., Ikejima and Dinarello [1985] *J. Leukocyte Biology* 37:714); other acute or chronic inflammatory disease states such as the inflammatory reaction induced by endotoxin (see, e.g., Habicht and Beck [1985] *J. Leukocyte Biology* 37:709); and other chronic inflammatory disease states such as tuberculosis (see, e.g., Chesque et al. [1985] J. Leukocyte Biology 37:690). Benjamin et al. ([1985] "Annual Reports in Medicinal Chemistry—20," Chapter 18, pp. 173–183, Academic Press, Inc.) disclose that excessive IL-1 production is implicated in psoriatic arthritis, Reiter's syndrome, rheumatoid arthritis, osteoarthritis, gout, traumatic arthritis, rubella arthritis, and acute synovitis.

Dinarello ([1985] *J. Clinical Immunol.* 5(5):287–297) reviews the biological activities which have been attributed to IL-1.

Another form of IL-1, the naturally-occurring receptor antagonist protein (IL-1ra) (Carter, D. B., M. R. Deibel, C. J. Dunn et aL [1990] *Nature* 344:633–638; Hannum, C. H., C. J. Wilcox, W. P. Arend et al. [1990] *Nature* 343:336–340; Seckinger, P. K. Williamson, J.-F. Balavoine et al. [1987] *J. Immunol.* 139:1541–1545) may play an important role in modulating the effects of IL-1. Interleukin-1 biological activity is initiated by interaction with either the type I or type II cellular IL-1 receptors (Dower, S. K., S. R. Kronheim, C. J. March et al. [1984] *J. Exp. Med.* 162:501; Sims, J. E., S. K. Dower [1990] *Year in Immunology* 6:112–126; Sims, J. E., C. J. March, D. Cosman et al. [1988] *Science* 241:585–588; Spriggs, M. K., P. J. Lioubin, J. Slack et al. [1990] *J. Biol. Chem.* 265:22499–22505), each of which possesses three immunoglobulin-fold extracellular ligand-binding domains. The IL-1ra also binds to IL-1 receptors, but this protein has not been reported to elicit biological responses (Dripps, D. J., B. J. Brandhuber, R. C. Thompson, S. P. Eisenberg [1991] *J. Biol. Chem.* 266:10331–10336). The three-dimensional structures of both IL-1α and IL-1β have been reported (Clore, G. M., P. T. Wingfield, A. M. Gronenbom [1991] *Biochemistry* 30:2315–2323; Driscoll, P. C., G. M. Clore, D. Marion et al. [1990] *Biochemistry* 29:3542–3556; Finzel et al., supra; Graves et al. [1990],supra; Priestle et al. [1988], supra; Priestle, J. P., Schar, H. P., M. G. Grutter [1990] *Cytokines and Lipocortins* 349:297–307) and both receptor types have been molecularly cloned and expressed (McMahan, C. J., J.

L. Slack, B. Mosely et al. [1991] *EMBO J.* 10:2821; Sims et al. [1988], supra; Spriggs et al., supra).

By changing the $R_{127}$ in β-strand 1 of the native IL-1β to a glycine, it has been determined that the receptor binding and biological activity domains of the protein are at least partially distinct. Others have subsequently reported similar effects resulting from mutating other amino acids located in the hydrogen-bonded antiparallel β-strand 1 and 12 of IL-1β (Ju, G., E. Labriolatompkins, C. A. Campen et al. [1991] *Proc. Natl. Acad. Sci. USA* 88:2658–2662; Young, P., V. Kumar, J. Lillquist et al. [1990] *Lymphokine Res.* 9:599). Ju et al., supra, also showed that the IL-1ra protein can be converted to a partial agonist by mutating a residue in a similar structural location.

It is known that in many cases that both cellular and/or humoral immune responses to an antigen administered to an animal can be enhanced or increased by immunizing the animal with the antigen in conjunction with some type of adjuvant. An adjuvant, in broad terms, may be thought of as a compound or composition which can enhance or amplify an animal's immune response (e.g., an increase in antibody titer) to an antigen or immunogen. Various adjuvants are known in the art, including Freund's (complete and incomplete), muramyl dipeptide (MDP), and alum.

Mucosal immunization typically induces a state of immunologic unresponsiveness known as "oral tolerance" or more correctly mucosally induced tolerance. The induction of the appropriate mucosal immune response to human pathogens (HIV, HSV, measles, mumps, RSV, etc.) may provide superior systemic immune responses for protection against infection. Mucosal immune responses have been reported to prevent infection while systemic immune responses usually resolve the infection (they do not prevent infection).

The most potent and best-studied mucosal adjuvant is cholera toxin (CT, Elson et al. [1994] in *Handbook of Mucosal Immunology, p* 391). However, CT is likely unsafe for use as a mucosal adjuvant in humans because as little as 5 micrograms (μg) of CT causes massive diarrhea when intragastrically administered to human volunteers (Levine et al. [1983] *Microbiological Reviews* 47:510). Moreover, in some cases the use of CT as a mucosal adjuvant in research animals has been associated with the production of antigen-specific IgE responses and lethal anaphylactic reactions. See, e.g., Snider et al. [1994] *J. Immunol* 153:647; Marinaro et al. [1995] *J. Immunol* 155:4621.

To repress the toxicity associated with toxin adjuvants, mutant CT, LT, and PT molecules have been produced that exhibit reduced or undetectable toxic activity while maintaining mucosal adjuvant activity (O'Hagan [1997] *Journal of Pharmacy and Pharmacology* 49:1). Although these molecules possess potent adjuvant activity with reduced toxicity, they maintain immunogenic properties when administered to experimental animals. See e.g. Douce et al. [1977] *Infection & Immunity* 65:2821. Thus, the immunogenicity of these mutant toxin molecules also prevents their widespread and repeated use as mucosal adjuvants in that pre-existing immunity to CT reduces their adjuvant activity (Wu et al. [1994] *Vaccine* 12:215).

PCT Publication No. WO 91/01143 to Pillai et al. describes interluekin (IL)-containing vaccine compositions which comprise a mixture of antigen and an adjuvant amount of an IL adsorbed onto a mineral in suspension, and a preservative. The mineral is described as preferably being alum. Alum is described as stabilizing the biological activity of the IL. Exemplary IL's includes IL-1α, IL-1β, IL-2, IL-3, IL-4, IL-5, IL-6 and IL-7. It is noted that in the absence of alum, IL's have short half lives. Carbohydrate-containing units found uniquely on cancer cells or found associated with allergens are particularly described antigens. However, the problems associated with oral or mucosally-induced tolerance of antigens are not addressed.

U.S. Pat. No. 5,334,379 issued to Pillai et al. on Aug. 2, 1994 describes cytokine and hormone carriers for conjugate vaccines. The antigens described in this patent are bound or genetically fused with a cytokine, lymphokine, hormone or growth factor having immunomodulating activity. Particularly contemplated antigens include the carbohydrate-containing antigens often present in bacteria. Exemplary cytokines, lumphokines and hormones include IL-1α, IL-1β, IL-2, prolactin, EGF, TGF, GM-CSF, GCSF, IGF-1, somatotropin, or insulin. The conjugates may be prepared by any of the known complex, biologically compatible methods for coupling carbohydrate-containing antigens or other antigens to carriers. Covalent coupling is described as a preferred method. Indeed, Examples 1 and 2 describe the elaborate reactions required to conjugate or bind the antigens to the cytokine, lumphokine, hormone or growth factor. However, the problems associated with oral or mucosally-induced tolerance of antigens are not addressed.

A recent review article by Kramer et al. (Kramer et al. [1995] entitled "Cytokine Mediated Effects in Mucosal Immunology" in *Immunology & Cell Biology* 73:389) discusses the role of IL-5, IL-6, and TGF-β in the induction of mucosal IgA responses. Particularly, this paper discussed published results from experiments done in mice lacking a functional IL-5 or IL-6 gene. It also discusses papers which describe the co-expression of IL-5 or IL-6 with vaccine antigen in a live vaccinia virus, and which describe that the co-expression of IL-5 or IL-6 enhances mucosal IgA responses. However, the article then suggests that complex delivery methods will be required to deliver the cytokines to the mucosa.

Another recent review article by O'Hagan entitled "Recent Advances in Vaccine Adjuvants for Systemic and Mucosal Adjuvants" in the *Journal of Pharmacy and Pharmacology* 49:1 (1997) discusses the state of the use of adjuvants for systemic and mucosal administration. This review article discusses a number of different adjuvants for use with mucosally administered vaccines including particulates (i.e. microspheres), oil-in-water emulsions, and mutated forms of heat-labile enterotoxin (LT) and cholera toxin (CT). But, this article does not mention the use of cytokines as mucosal vaccine adjuvants.

A journal article by Lin et al. entitled "Present Status of the Use of Cytokines as Adjuvants with Vaccines to Protect Against Infectious Diseases" in *Clinical Infectious Diseases* 21:1439 (1995) discusses the use of select cytokines (IL-1, IL-2, IL-3, IL-4, IL-6, IL-7, and IL-12; tumor necrosis factor (TNF); interferon; and GM-CSF as adjuvants. But, the use of cytokines as mucosal vaccine adjuvants is not suggested in this article.

A journal article by Nash et al. entitled "Recombinant Cytokines as 20 Immunological Adjuvants", *Immunology and Cell Biology* 71:367 (1993) discusses the use of recombinant ovine IL-2, IL-1α and tumor necrosis factor-α (TNF-α) as adjuvants. The formulation of IL-1α with aluminum hydroxide (alum) is mentioned for use as an adjuvant capable of enhancing secondary humoral responses. But, there is no suggestion of mucosal administration of IL-1α.

More recently, polypeptides and small peptides have been used as adjuvants. U.S. Pat. No. 5,503,841 discloses the use of interleukin-2 (IL-2) as an adjuvant with vaccines. U.S.

Pat. No. 5,206,014 discloses the use of a peptide fragment of human IL-1β as an adjuvant with antigens having low immunogenicity. However, systemic administration of immunomodulators, such as interleukins, as adjuvants can result in an overstimulation or dysfunctional activation of the immune system of the animal. Systemic in vivo administration of IL-1β has been associated with unwanted side effects, including fever and nausea.

There has been a report that recombinant ovine interleukin-1β has adjuvant activity when administered intramuscularly to mice or sheep (Vaccine 13:1277–1287). However, this study did not address the use of IL-1 as a mucosal adjuvant. It has also been reported that Interleukin 1 is an effective adjuvant for mucosal and systemic immune responses when coadministered with protein immunogens (Staats, H. F. and F. A. Ennis, Jr. [1999] J. of Immunology 162:6141–6147). Presently, the only mucosal adjuvants that have worked well include bacterial toxins such as cholera toxin, heat-labile toxin, or pertussis toxin. A number of groups are genetically modifying the bacterial toxins so that they maintain adjuvant activity in the absence of toxin activity. However, a foreign protein must still be used as an adjuvant.

There remains a need in the art for adjuvants that stimulate or activate appropriate cells of the immune system without overstimulation or dysfunction.

BRIEF SUMMARY OF THE INVENTION

The present invention pertains to compositions and methods useful as vaccine adjuvants. In a preferred embodiment, the subject invention provides adjuvant compositions comprising a human IL-1β mutein. More specifically, the adjuvants of the subject invention preferably comprise IL-1β muteins wherein a positively charged residue (arginine or lysine) is replaced with any of the other 17 natural amino acids.

The IL-1β vaccine compositions preferably further comprise an antigen, such as whole inactivated or attenuated virus, recombinant or synthetic peptides, and/or other antigenic materials. These IL-1β muteins have reduced biological activity, as compared to the parent molecule, without loss of receptor binding affinity.

The present invention also pertains to the use of IL-1 muteins for use as a means to increase immune responses in a patient. In an exemplified embodiment of the present invention, muteins of IL-1β can be used as an immunomodulator for increasing immune responses.

In accordance with the present invention, a method of eliciting an immune response against an antigen in a vertebrate subject is provided. In a specific embodiment, the method comprises the steps of providing an antigen-adjuvant composition comprising the antigen and a substantially non-toxic adjuvant molecule or molecules, and administering said antigen-adjuvant composition to the vertebrate subject, whereby an immune response is elicited. Preferably, the immune response comprises a systemic and/or mucosal immune response.

The IL-1β mutein adjuvant of the subject invention can be administered in the presence or absence of a vaccine antigen and either prior to or subsequent to vaccine antigen administration.

BRIEF DESCRIPTION OF THE DRAWINGS

FIG. 1. Schematic representation of human IL-1β cDNA and deletion constructs. The interleukin-1β cDNA was subcloned into plasmid pSP64 (Promega Biotec). The SP6 promoter is represented by the filled box, and the direction of transcription is noted by the horizontal arrow. The letter U symbolizes the untranslated leader sequence, which in these experiments was either the native IL-1β sequence or that of alfalfa mosaic virus RNA 4. The open rectangle represents the IL-1β precursor coding region, within which are shown regions of homology (a–e). Relevant restriction enzyme sites used to make the deletion constructs are shown above the IL-1β sequence, and the location of the amino terminus of the processed mature IL-1β protein ($Ala_{117}$) is denoted by the vertical arrow. Lower, schematic diagrams of several deletion constructs. Terminal amino acids are indicated by capital letters and subscript numbers (M, methionine; A; alanine; S; serine; T, threonine). Amino acids derived from vector sequence rather than the IL-1β coding region are denoted by diagonal lines positioned at either end of the construct.

FIG. 2. Biological activities of IL-1β proteins. Reticulocyte translation mixtures were incubated and assayed in the thymocyte co-stimulation assay as described previously (Jobling et al., 1988). The results are presented as [$^3$H] thymidine incorporation (counts/minute) at various final dilutions of the translation mixtures.

DETAILED DISCLOSURE OF THE INVENTION

The subject invention pertains to the use of IL-1 muteins as adjuvants. In a preferred embodiment of the subject invention, the adjuvant is a mutein of IL-1 β.

The IL-1 mutein compositions described herein can be advantageously used in conjunction with an antigenic or immunogenic composition for the preparation of a vaccine. Such a composition, when administered to a person or animal, increases immune responses to the administered vaccine antigen as compared to vaccine antigen when administered alone, but without overstimulation or dysfunctional activation of the immune system normally associated with the administration of wild type IL-1.

Mutein adjuvants of the present invention can optionally include or be used in conjunction with an antigen, such as whole inactivated or attenuated virus, recombinant or synthetic polypeptides or peptides, haptens, and other antigenic or immunogenic materials. Using the methods and materials of the present invention provides for presentation of IL-1β mutein, either in the presence or absence of an antigen, to antigen presenting cells of the immune system but with reduced biological activity and, hence, reduced side effects.

The subject invention also concerns methods for enhancing immune responses in an animal or human by administering an effective amount of an IL-1 mutein to the person or animal in need of such treatment. In a preferred embodiment, an IL-1β mutein can be used as an adjuvant to increase immune responses to an immunogen or antigen, such as those used in vaccine compositions, without the side effects associated with administration of wild type IL-1β, such side effect being the overstimulation or dysfunctional activation of the immune system. Preferably, the vaccine compositions of the subject invention can comprise whole inactivated or attenuated virus, subunits of viral components, recombinant or synthetic polypeptides or peptides, haptens, and other antigenic or immunogenic materials. The IL-1β mutein can be administered in the presence or absence of an antigen. Thus, the IL-1β mutein of the subject invention can also be administered either prior to or subsequent to antigen administration. Preferably, the IL-1β mutein is administered in a pharmaceutically acceptable carrier.

The amount of IL-1β mutein to be administered according to the methods of the subject invention can be readily determined by a person skilled in the art having the benefit of the instant disclosure.

The mutein adjuvant of the present invention can be administered to an animal or human parenterally, for example, by intramuscular or subcutaneous injection.

The methods and adjuvant of the present invention can be used with vaccines directed to treating or immunizing animals and/or humans against bacteria, viruses, tumor cells, fungus, and parasites.

All references cited herein are incorporated by reference.

The conversion of IL-1 molecules by mutation of specific residues gives muteins having utility as adjuvants but, advantageously, have reduced side effects. Specifically disclosed is a human IL-1β mutein, as described in U.S. Pat. No. 5,286,847, which is incorporated herein by reference. Table 1 shows that this mutant binds as efficiently as the native mature IL-1β protein (i.e., the protein derived from residues 117–269 of the precursor).

IL-1β peptides were synthesized by in vitro translation in the presence of [$^{35}$S]methionine and incubated with EL.4 cells at 4RC. The equilibrium dissociation constants were determined by Scatchard plot analysis (Jobling et al., 1988). For comparison, the dissociation constants of proIL-1β and two IL-1β deletion mutants are also shown. The right column illustrates the receptor binding affinities expressed in relation to mature wild-type IL-1 β (100%).

TABLE 1

Dissociation constants and relative binding of IL-1β peptides.

| Peptide | $K_d$ | Relative binding |
|---|---|---|
| Mature IL-1β (117-269) | $1.01 \times 10^{-9}$ | 100 |
| Mature $R_{127} \rightarrow G_{127}$ | $1.08 \times 10^{-9}$ | 107 |

Figure 2:
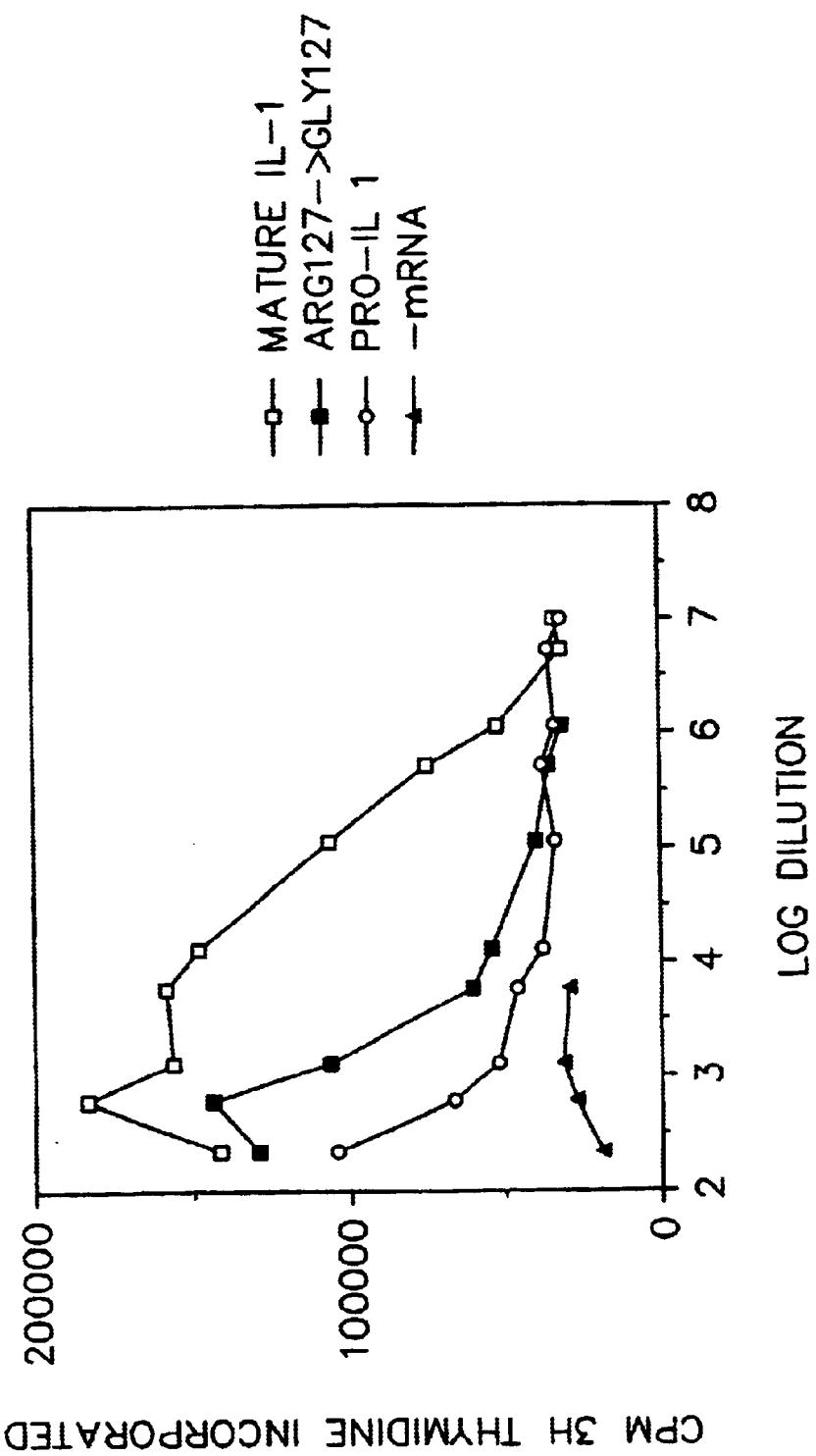

FIG. 2 shows that this same mutant induces only 1% of the biological activity induced by the mature IL-1 β. Therefore, the substitution of a glycine for an arginine at position 127 of human IL-1 β generates a molecule which binds to the IL-1 receptor without inducing a strong activity, thus interfering with the binding of active forms of IL-1 and thereby reducing the amount of IL-1 bioactivity.

The muteins of the subject invention are molecules which interact with, or cause an interaction with, an IL-1 receptor to an extent which is sufficient to elicit and/or augment a favorable immune response but wherein the mutein results in no side effects or side effects which are reduced compared to the side effects which result from administration of the wild-type molecule. In a preferred embodiment, the mutein adjuvant of the subject invention is IL-1 β having a mutation wherein the arginine which naturally exists at position 127 is replaced with glycine.

As used herein, the term "immune system" includes all the cells, tissues, systems, structures and processes, including non-specific and specific categories, that provide a defense against "non-self" molecules, including potential pathogens, in a vertebrate subject.

As is well known in the art, the non-specific immune system includes phagocytositic cells such as neutrophils, monocytes, tissue macrophages, Kupffer cells, alveolar macrophages, dendritic cells and microglia. The specific immune system refers to the cells and other structures that impart specific immunity within a host. Included among these cells are the lymphocytes, particularly the B cell lymphocytes and the T cell lymphocytes. These cells also include natural killer (NK) cells. Additionally, antibody-producing cells, like B lymphocytes, and the antibodies produced by the antibody-producing cells are also included within the term "immune system."

The term "substantially non-toxic" is meant to refer to adjuvant molecules which cause few detrimental effects when administered to a vertebrate subject. Examples of detrimental effects include the nausea and anaphylactic shock observed through the use of standard adjuvants like cholera toxin. Thus, the term "substantially non-toxic" can be quantified by comparison to cholera toxin as a known standard. Further, "substantially non-toxic" means without prolonged or major side effects including weight loss and prolonged fever, and including, but not limited to, the flu-like symptoms such as fever, prolonged muscle or joint pain, or hypotension (shock), that are observed with some vaccinations currently used in the art.

The terms "mucosal administration" and "intramucosal administration" are meant to refer to a mode of administration whereby antigen-adjuvant composition according to the present invention is administered in a manner such that initial contact occurs in mucosal tissue of the vertebrate subject. Examples of mucosal tissue include the nasal membranes, vaginal membranes, rectal membranes and gastric membranes. Thus, contemplated administration techniques according to the methods of the present invention include intranasal administration, intravaginal administration and intrarectal administration, among other intramucosal administration techniques.

The term "biological activity" is meant to refer to a molecule having a biological or physiological effect in a vertebrate subject. Adjuvant activity is an example of a biological activity. Activating or inducing production of other biological molecules having adjuvant activity is also a contemplated biological activity.

The term "adjuvant activity" is meant to refer to a molecule having the ability to enhance or otherwise modulate the response of a vertebrate subject's immune system to an antigen.

The term "immune response" is meant to refer to any response to an antigen or antigenic determinant by the immune system of a vertebrate subject. Exemplary immune responses include humoral immune responses (e.g. production of antigen-specific antibodies) and cell-mediated immune responses (e.g. lymphocyte proliferation), as defined herein below.

The term "systemic immune response" is meant to refer to an immune response in the lymph node-, spleen-, or gut-associated lymphoid tissues wherein cells, such as B lymphocytes, of the immune system are developed. For example, a systemic immune response can comprises the production of serum IgG's. Further, systemic immune response refers to antigen-specific antibodies circulating in the blood stream and antigen-specific cells in lymphoid tissue in systemic compartments such as the spleen and lymph nodes. In contrast, the gut-associated lymphoid tissue (GALT) is a component of the mucosal immune system since antigen-specific cells that respond to gut antigens/ pathogens are induced and detectable in the GALT.

The term "mucosal immune response" is meant to refer to an immune response in the mucosal tissues of a vertebrate subject. The mucosal immune response can comprise production of IgA's, particularly secretory IgA's, in mucosal tissue at a location in the vertebrate subject away from the site of mucosal administration of the antigen-adjuvant composition according to the present invention.

The terms "humoral immunity" or "humoral immune response" are meant to refer to the form of acquired immunity in which antibody molecules are secreted in response antigenic stimulation.

The terms "cell-mediated immunity" and "cell-mediated immune response" are meant to refer to the immunological defense provided by lymphocytes, such as that defense provided by T cell lymphocytes when they come into close proximity to their victim cells. A cell-mediated immune response also comprises lymphocyte proliferation. When "lymphocyte proliferation" is measured, the ability of lymphocytes to proliferate in response to specific antigen is measured. Lymphocyte proliferation is meant to refer to B cell, T-helper cell or CTL cell proliferation.

The term "CTL response" is meant to refer to the ability of an antigen-specific cell to lyse and kill a cell expressing the specific antigen. Standard, art-recognized CTL assays are performed to measure CTL activity.

Combinations of cytokines are also contemplated for use in accordance with the methods of the present invention. Additionally, a particularly contemplated embodiment comprises the use of IL-12 and IL-18 in combination as a mucosal adjuvant in accordance with the methods of the present invention. When cytokines are used in combination, contemplated dosage ranges comprise about 0.3 $\mu$/ml to about 50 $\mu$g/ml, with respect to each cytokine. Additional contemplated dosages ranges are described below.

The antigen-adjuvant compositions are preferably administered in a pharmaceutically acceptable vehicle. The preferred vehicle is physiological saline; but, distilled water may also be used as a vehicle. More preferably, the antigen-adjuvant composition is free of mineral adjuvants, preservatives or stabilizers, such as alum. Also preferably, the antigen-adjuvant composition is not conjugated. Rather, the antigen and adjuvant are simply dissolved and/or suspended in the vehicle.

In accordance with the present invention, antigen is administered in combination with a substantially non-toxic, biologically active adjuvant preferably at weekly or biweekly intervals for a total of three (3) immunizations in order to stimulate a "protective" immune response. A protective immune response is an immune response sufficient to protect the immunized organism against toxic products of bacteria (tetanus toxin, cholera toxin, *E. coli* labile toxin, diphtheria toxin, pertussis toxin) as well as against productive infection by a particular pathogen or pathogens to which the vaccine is directed.

Stated differently, the antigen-adjuvant composition may optionally be administered once a week over a period of one to three weeks or once every two weeks over a period of two to six weeks. Alternatively, the antigen-adjuvant composition may be administered once during a first week, and then antigen only may be administered as a booster immunization once a week over a period of one to two weeks following the first week. Further, the antigen-adjuvant composition may optionally administered as a booster immunization once every two weeks over a period of two to four weeks following the first biweekly period.

The adjuvants are present preferably in an amount ranging from about 10 to about 1000 micrograms per kilogram body weight of the vertebrate subject. More preferably, the adjuvant is present in the antigen-adjuvant composition in an amount ranging from about 50 to about 500 micrograms per kilogram body weight of the vertebrate subject. Even more preferably, the adjuvant is present in the antigen-adjuvant composition in an amount ranging from about 60 to about 200 micrograms per kilogram body weight of the vertebrate subject.

The amount of adjuvant employed in the methods of the present invention will vary depending upon the identity of the antigen employed. Adjustment and manipulation of the adjuvant dosage ranges described above for adaptation to a variety of antigens is within the ability of those skilled in the art. The adjuvant-antigen compositions, or vaccines of the present invention are intended for use in the treatment of vertebrate subjects, including both immature and adult warm-blooded animals. Exemplary warm blooded vertebrate subjects include mammals and birds. Mammals are preferred subjects, with humans comprising a most preferred subject. Indeed, in accordance with the present invention, any vaccine against infection can be formulated for administration to humans or other warm blooded vertebrate animals. Further, the use of the present methods is not limited to prophylactic applications; therapeutic applications are also contemplated (e.g., AIDS prophylaxis and therapy), as well as immune focusing to alter growth, productivity or reproduction.

Suitable antigens which can be used in the antigen-adjuvant compositions of the present invention include soluble antigens, such as proteins, peptides, hormones and glycoproteins. Antigens of particular interest are viral, fungal, parasite or bacterial antigens, allergens, auto-immunity related antigens, or tumor-associated antigens. The antigens can be obtained from natural sources or they can be produced by recombinant DNA technology or by other artificial means.

Among the bacterial antigens of interest are those associated with the human and animal bacterial pathogens including, but not limited to for example, typable and nontypable *Haemophilus influenzae, Escherichia coli, Neisseria meningitidis, Streptococcus pneumoniae, Streptococcus pyogenes, Branhamella catarrhalis, Vibrio cholerae, Corynebacteria diphtheriae, Neisseria gonorrhoeae, Bordetella pertussis, Pseudomonas aeruginosa, Staphylococcus aureus, Klebsiella pneumoniae* and *Clostridium tetani*. Some specific bacterial antigens include bacterial surface and outer membrane proteins (e.g. from *Haemophilus influenzae, Neisseria meningitidis, Neisseria gonorrhoeae* or *Branhamella catarrhalis*) and bacterial surface proteins (e.g. the M protein from *Streptococcus pyogenes*.).

Viral antigens from pathogenic viruses include but are not limited to, HIV (types 1 and II), human T-cell leukemia virus (types I, II and III), RSV, hepatitis A, hepatitis B, hepatitis C, non-A and non-B hepatitis virus, herpes simplex virus (types I and II), cytomegalovirus, influenza virus, parainfluenza virus, poliovirus, rotavirus, coronavirus, rubella virus, measles virus, varicella, Epstein Barr virus, adenovirus, papilloma virus and yellow fever virus.

Several specific viral antigens of these pathogenic viruses include the F protein (described in WO 89/02935 by Paradiso et al.) and the N and G proteins of RSV; VP4 (previously known as VP3); VP6 and VP7 polypeptides of rotavirus; envelope glycoproteins of HIV; and the surface and presurface antigens of hepatitis B and herpes glycoproteins B and D.

Fungal antigen that can be those derived from fungi including but not limited to Candida spp. (e.g., albicans), Cryptococcus spp. (e.g., neoformans), Blastomyces spp. (e.g., immitis), Paracoccidroides spp. (e.g., brasiliensis) and Aspergillus spp. Examples of parasite antigens include, but are not limited to, Plasmodium spp., Eimeria spp., Schistosoma spp., Trypanosoma spp., Babesia spp., Leishmania spp., Cryptosporidia spp., Toxoplasma spp. and Pneumocystis spp.

Also of interest are various antigens associated with auto-immune diseases, such as rheumatoid arthritis and lupus erythematosus.

Other applications may also include the elicitation of an immune response to stimulate or inhibit the stability or interaction of cellular modifiers, including hormones with their corresponding receptors or binding components. In this fashion, the immune response can be used to inhibit/enhance growth, reproduction, differentiation, and overall performance.

It is to be understood from the above discussion, that the use of the term antigen is meant to imply either the whole antigen or one of its determinants. The foregoing list of antigens is for exemplary purposes only. Additional antigens which can be used in the antigen-adjuvant compositions of the present invention are readily ascertained by one skilled in the art. Further, the antigen-adjuvant formulations of the present invention are stable for a period of time sufficient to allow the manufacture, shipment and storage of the vaccine formulations.

Materials and Methods

Plasmid Constructions.

The plasmid constructs used to generate IL-1β mRNAs for in vitro translation are diagramed in FIG. 1. The IL-1β cDNA was subcloned into plasmid pSP64 (Promega Biotec), and the 86-base pair IL-1β mRNA untranslated leader (UTL) sequence was excised and replaced with the 37-base pair UTL of alfalfa mosaic virus RNA 4. As described elsewhere (Jobling, S. A., L. Gehrke [1987] Nature 325:622–625), the translational efficiency of the IL-1β mRNA is increased by replacing the native UTL with that of the plant viral RNA. The noncoding AMV RNA 4 UTL oligonucleotide was ligated to the IL-1β cDNA at the NcoI site (CCATGG) situated at the initiating ATG codon; therefore, the amino acid sequence of proIL-1β is not altered. Deletion constructs can be generated either by cleaving the IL-1β cDNA sequence at appropriate restriction enzyme sites shown in FIG. 1, followed by ligation of the termini to maintain the translational reading frame, or by use of recombinant PCR techniques well known in the art and as described in great detail in Higuchi, R. (1990) "Recombinant PCR," In M. A. Innis et al. (eds.), PCR Protocols: A Guide to Methods and Applications, Academic Press, Inc., San Diego, pp. 177–183. In Higuchi's technique, DNA primers 24 nucleotides long can be used to flank the site to be deleted, and then amplified by upstream and downstream additional primers.

The numbers to the right of FIG. 1 refer to amino acid positions, using proIL-1β (269 amino acids) as reference. In all of the IL-1 (117–269) constructs, it is necessary to add a methionine (ATG) codon to initiate translation, and the added methionine is noted in the label and separated from the numbered amino acid positions (e.g., M, 117–269). The IL-1-(M, 117–269) construct was generated by ligating a synthetic 60-base pair oligonucleotide at the HindIII site of the IL-1β cDNA. All amino acid substitutions at positions 117, 118, 125, and 127 described herein are generated as variations on this 60-bp oligonucleotide. With the exception of SP6 IL-1β, all messenger RNAs transcribed from the constructs shown in FIG. 1 contain the alfalfa mosaic virus RNA 4 UTL.

Transcription of IL-1β Plasmid DNAs.

Plasmid DNAs were linearized with BamHI and transcribed as described previously (Jobling & Gehrke [1987], supra).

In Vitro Translations.

Capped SP6 mRNAs were transcribed from linearized DNAs, and low molecular-weight materials were removed by passing the DNAse-treated transcription reaction through two successive Sephadex G-50 spun columns. The eluate was then extracted twice with phenol/chloroform, once with ether, and nucleic acids were precipitated with ethanol from 2.5 M ammonium acetate. Translations were performed essentially according to the manufacturer's recommendations. Wheat-germ translations were prepared using 5 µl of nuclease-treated wheat-germ extract (Amersham) in a total volume of 10 µl containing 105 mM potassium acetate, 2 mCi ml$^{-1}$ $^{35}$S-methionine, and the reaction mixture was incubated for 1 hour at 30RC.

The biological activity of IL-1β mutant proteins substituted with lysine (K), glutamic acid (E), tryptophan (W), and alanine (A) at the same site (position 127) as the glycine (G) substitution have also been studied. While the biological activity of the $R_{127} \rightarrow G_{127}$ mutein was greatly diminished, the K, E, W, and A substitutions had no significant effect upon the biological activity of the mutant proteins. The fact that the 127-position can tolerate all manner of replacements possessing a side-chain Cβ atom, including alanine, which is incapable of forming side-chain hydrogen bonds or salt bridges, shows that the packing of amino acid residues plays a central role in maintaining the IL-1β function. $R_{127}$ structurally supports other residues which define a cleft in the IL-1 molecule. Part of this cleft has at its center the aspartic acid residue ($D_{261}$) which has been mutated to generate a protein which binds receptor but has diminished bioactivity (Clore et al, supra; Ju et al., supra). This "$D_{261}$ cleft" contains a cluster of amino acids which are conserved in IL-1α and IL-1β proteins from five different species, and which are important for initiating the IL-1 biological response. Molecular modeling shows that by introducing the glycine, lacking a β-carbon, the structure of the protein is perturbed through collapse of β-strand 1 into the hydrated space bounded by strands 1, 2, and 4. This loss of structural support for the $D_{261}$ cleft is related to the loss of late signal transduction observed using the $R_{127}$→$G_{127}$ mutant protein.

Following are examples which illustrate procedures for practicing the invention. These examples should not be construed as limiting. All percentages are by weight and all solvent mixture proportions are by volume unless otherwise noted.

EXAMPLE 1

Synthesis of IL-1β Proteins

IL-1β proteins can be synthesized by in vitro translation of SP6 or T7 messenger RNAs. In vitro protein synthesis can be performed as described previously (Jobling et al., 1988; Jobling, S. A., L. Gehrke [1987] *Nature* 325:622–625). The translational efficiency of all construct mRNAs was increased by replacing the untranslated leader sequence of the IL-1β mRNA with that of alfalfa mosaic virus RNA (Jobling et al., 1988; Jobling et al., 1987). The IL-1β protein translation products specifically exemplified herein contain the amino-terminal methionine residue added during initiation of protein synthesis. The biological activity of the translation products was tested by quantitating [$^3$H] thymidine incorporation by helper T-cells (D10.G4.1) (Kaye, Y., S. Porcelli, J. Tite, B. Jones, C. A. Janeway [1983] *J. Exp. Med.* 158:836–856) incubated in the presence of diluted translation reaction mixtures (FIG. 2). The results demonstrate that the half maximal biological activity of the $R_{127}$→$G_{127}$ mutant protein is greater than that of proIL-1β, but at least 100-fold less than that of the wild-type mature IL-1 β.

EXAMPLE 2

Receptor Binding Characteristics

The receptor binding characteristics of the $R_{127}$→$G_{127}$ mutant protein were determined by Scatchard analysis and by sodium dodecyl sulfate (SDS) polyacrylamide gel analysis of specifically bound proteins (Dower et al., 1986;

Jobling et al., 1988; Mosley et al. [1987] *J. Biol. Chem.* 262:2941–2944). For the polyacrylamide gel analysis, IL-1β proteins were labeled with [$^{35}$S]methionine during in vitro translation before cell surface receptor binding assays using EL4 6.1 C10 murine thymoma cells (Jobling et al., 1988; Mosley et al. [1987] *Proc. Natl. Acad. Sci. USA*, supra; MacDonald, H. R., R. K. Lees, C. Bron [1985]*J. Immunol.* 135:3944). The intensity of the bands representing bound native mature IL-1β and bound $R_{127} \rightarrow G_{127}$ mutant IL-1β (FIG. 3) suggested that the receptor binding properties were similar despite the observation that the bioactivities of the proteins were unequal (FIG. 2). Equilibrium binding experiments and Scatchard plot data (Table 1) confirmed the equivalence of binding constants.

EXAMPLE 3

Use of IL-1β Mutein as an Adjuvant

Mice were immunized with various compositions to evaluate the adjuvant effect of mutant IL-1β compared to wild-type IL-1β and alum. The mutant had a glycine instead of argine at position 127.

Experimental Design:

| Group 1: | 50 μg tetanus toxoid (TT) nasally |
|---|---|
| Group 2: | 1 μg CISTRON IL-1β and 50 μg TT, nasally |
| Group 3: | 50 μg TT and ALUM administered subcutaneously |
| Group 4: | 25 μg mutant IL-1β and 50 μg TT, nasally |
| Group 5: | 5 μg mutant IL-β and 50 μg TT, nasally |
| Group 6: | 1 μg mutant IL-β and 50 μg TT, nasally |

Subcutaneously immunize with 200 μl per mouse

Intranasally immunize with 15 μl per mouse (7.5 μl per nostril)

Immunize all groups on day 0, 21, 42.

Adverse Effects

Body weight was monitored the day of immunization and the day after immunization as an indicator of an adverse effect of the IL-1 β.

Immune Responses

Serum anti-TT IgG and IgA responses were monitored to determine if the mutant IL-1β exhibits adjuvant activity. The results are shown in Table 2 and 3.

TABLE 3

Serum Anti-Tetnus Toxoid Responses After Nasal Immunization with Tetanus Toxoid ± IL-1β, mutant IL-1β or Subcutaneous Immunization with Tetanus Toxoid and Alum

| | Serum Anti-Tetanus Toxoid End-Point Titer | |
|---|---|---|
| Group | IgG | IgA |
| 1 | 1:9,741 x/+ 2.39 | 1:5.7 x/+ 32 |
| 2 | 1:114,105 x/+ 2.47 | 1:1,552 x/+ 1.85 |
| 3 | 1:150,562 x/+ 1.36 | <1:256 |
| 4 | 1:172,951 x/+ 1.46 | 1:1,351 x/+ 1.46 |
| 5 | 1:262,144 x/+ 1.76 | 1:3,444 x/+ 2.39 |
| 6 | 1:301,124 x/+ 1.78 | 1:1,351 x/+ 1.86 |

Conclusions

1. Mutant IL-1β possesses mucosal adjuvant activity comparable to native IL-1 β.
2. When compared to native IL-1β on a molar basis, mutant IL-1β does not cause weight loss to the extent observed for native IL-1 β.
3. Nasal immunization with TT and IL-1β or mutant IL-1β induces serum anti-TT IgG responses comparable to those induced by subcutaneous immunization with TT adsorbed to alum.

EXAMPLE 4

Formulations

Vaccines can be prepared by procedures well known in the art. For example, such vaccines can be prepared as injectables, e.g., liquid solutions or suspensions. Solid forms for solution in, or suspension in, a liquid prior to injection also can be prepared. Optionally, the preparation also can be emulsified. The mutein adjuvant and active antigenic ingredient or ingredients can be mixed with excipients which are pharmaceutically acceptable and compatible with the active ingredient. Examples of suitable excipients are water, saline, dextrose, glycerol, ethanol, or the like, and combinations thereof. In addition, if desired, the vaccine can contain minor amounts of auxiliary substances such as wetting or emulsifying agents, pH buffering agents, or adjuvants such as aluminum hydroxide or muramyl dipeptide or variations thereof. Also, cholera toxin subunit B or other agents which stimulate antibody production at mucosal sites can be used.

TABLE 2

Body Weight After Nasal Immunization with TT + IL-1β, TT + mutant IL-1β or Subcutaneous Immunization with TT and Alum

| | Body Weight (grams) | | | | | |
|---|---|---|---|---|---|---|
| Group | Day 0 | Day +1 (change from Day 0) | Day +21 | Day +22 (change from Day 21) | Day +42 | Day +43 (Change from Day 42) |
| 1 | 17.35 ± 0.81 | 17.81 ± 0.65 (+0.46) | 19.2 ± 0.54 | 19.39 ± 0.48 (+0.18) | 20.63 ± 0.27 | 20.64 ± 0.13 (+0.01) |
| 2 | 17.96 ± 0.98 | 17.57 ± 1.33 (−0.39) | 19.85 ± 1.31 | 18.91 ± 0.36 (−0.94) | 20.72 ± 1.17 | 18.79 ± 1.00 (−1.93) |
| 3 | 16.81 ± 1.46 | 17.15 ± 1.65 (+0.342) | 18.21 ± 1.85 | 19.04 ± 1.47 (+0.834) | 20.54 ± 1.18 | 20.81 ± 0.87 (+0.27) |
| 4 | 16.91 ± 1.06 | 16.2 ± 1.6 (−0.69) | 18.83 ± 1.51 | 18.28 ± 1.63 (−0.552) | 19.84 ± 1.11 | 18.42 ± 0.89 (−1.42) |
| 5 | 17.53 ± 1.64 | 17.49 ± 1.39 (−0.04) | 19.08 ± 1.67 | 19.05 ± 1.56 (−0.035) | 19.49 ± 1.39 | 18.83 ± 1.58 (−0.66) |
| 6 | 17.63 ± 1.58 | 17.75 ± 1.38 (+0.126) | 19.54 ± 0.85 | 19.17 ± 0.91 (−0.37) | 19.87 ± 2.77 | 19.79 ± 3.0 (−0.08) |

In the case of peptides, coupling to larger molecules such as KLH or tetanus toxoid sometimes enhances immunogenicity. Vaccines are conventionally administered parenterally, by injection, for example, either subcutaneously or intramuscularly. Additional formulations which are suitable for other modes of administration include suppositories and, in some cases, oral formulations. For suppositories, traditional binders and carriers include, for example, polyalkalene glycols or triglycerides. Suppositories can be formed from mixtures containing the active ingredient in the range of about 0.5% to about 10%, preferably about 1 to about 2%. Oral formulations can include such normally employed excipients as, for example, pharmaceutical grades of mannitol, lactose, starch, magnesium stearate, sodium saccharine, cellulose, magnesium carbonate, and the like. These compositions can take the form of solutions, suspensions, tablets, pills, capsules, sustained release formulations or powders and contain from about 10% to about 95% of active ingredient, preferably from about 25% to about 70%.

The compounds can be formulated into the vaccine as neutral or salt forms. Pharmaceutically acceptable salts include the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

A vaccine of the subject invention can be administered in a manner compatible with the dosage formulation, and in such amount as will be therapeutically effective and immunogenic. The quantity to be administered can depend on the subject to be treated and the degree of protection desired. Advantageously, methods known to promote mucosal immunity can be combined with systemic immunity promoters to maximize immune responses. Suitable regimes for initial administration and booster shots are also variable, but are typified by an initial administration followed in one or two week intervals by a subsequent injection or other administration.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A composition for stimulating immune response in a subject comprising:

an antigen, and a mutein of human interleukin-1β (IL-1 β) in which the arginine at position 127 of precursor IL-1 β has been replaced with another amino acid, wherein the IL-1β mutein has reduced toxicity to a human compared to the corresponding wild-type IL-1β.

2. The composition according to claim 1 wherein the arginine at position 127 of the precursor IL-1β has been replaced with glycine.

3. A composition for stimulating an immune response in a subject comprising an antigen, and a mutein of human interleukin-1β (IL-1β) in which the arginine at position 11 of mature IL-1β has been replaced with another amino acid, wherein the IL-1β mutein has reduced toxicity to a human compared to the corresponding wild-type IL-1β.

4. The composition according to claim 3 wherein the arginine at position 11 of the mature IL-1β has been replaced with glycine.

* * * * *